United States Patent
Kwan et al.

(10) Patent No.: US 7,942,873 B2
(45) Date of Patent: May 17, 2011

(54) CAVITY ABLATION APPARATUS AND METHOD

(75) Inventors: Harry Kwan, Fremont, CA (US); Robert Pearson, San Jose, CA (US); Darrin Uecker, San Mateo, CA (US); John Zepeda, Los Altos, CA (US)

(73) Assignee: AngioDynamics, Inc., Latham, NY (US)

( * ) Notice: Subject to any disclaimer, the term of this patent is extended or adjusted under 35 U.S.C. 154(b) by 934 days.

(21) Appl. No.: 11/388,724

(22) Filed: Mar. 24, 2006

(65) Prior Publication Data

US 2006/0259027 A1 Nov. 16, 2006

Related U.S. Application Data

(60) Provisional application No. 60/665,407, filed on Mar. 25, 2005.

(51) Int. Cl.
*A61B 18/18* (2006.01)
(52) U.S. Cl. .......................................... 606/45; 606/41
(58) Field of Classification Search .................. 606/33, 606/41, 45, 49
See application file for complete search history.

(56) References Cited

U.S. PATENT DOCUMENTS

| | | | |
|---|---|---|---|
| 5,536,267 A | 7/1996 | Edwards et al. | |
| 5,540,737 A | 7/1996 | Fenn | |
| 5,590,655 A | 1/1997 | Hussman | |
| 5,672,173 A | 9/1997 | Gough et al. | |
| 5,683,384 A | 11/1997 | Gough et al. | |
| 5,728,143 A | 3/1998 | Gough et al. | |
| 5,800,378 A * | 9/1998 | Edwards et al. | 604/22 |
| 5,823,956 A * | 10/1998 | Roth et al. | 600/374 |
| 5,855,576 A | 1/1999 | LeVeen et al. | |
| 5,868,673 A | 2/1999 | Vesely | |
| 5,980,517 A | 11/1999 | Gough | |
| 6,003,517 A | 12/1999 | Sheffield et al. | |
| 6,059,780 A | 5/2000 | Gough et al. | |
| 6,258,087 B1 * | 7/2001 | Edwards et al. | 606/41 |
| 6,261,241 B1 | 7/2001 | Burbank et al. | |
| 6,335,028 B1 * | 1/2002 | Vogel et al. | 424/422 |
| 6,336,926 B1 * | 1/2002 | Goble | 606/34 |
| 6,375,634 B1 | 4/2002 | Carroll | |
| 6,470,217 B1 | 10/2002 | Fenn et al. | |
| 6,494,844 B1 | 12/2002 | Van Bladel et al. | |
| 6,514,250 B1 | 2/2003 | Jahns et al. | |
| 6,652,518 B2 | 11/2003 | Wellman et al. | |
| 6,690,976 B2 | 2/2004 | Fenn et al. | |
| 6,869,430 B2 | 3/2005 | Balbierz et al. | |

(Continued)

OTHER PUBLICATIONS

Singletary, *Breast Cancer*, 10(1):4-9, 2003, abstract only.

(Continued)

*Primary Examiner* — Linda C Dvorak
*Assistant Examiner* — Jaymi Della
(74) *Attorney, Agent, or Firm* — Harry K. Ahn; Abelman Frayne & Schwab

(57) ABSTRACT

Ablation devices and associated methods are provided for use in ablating the margin of a cavity such as a surgical or body cavity. The ablation apparatus includes an integral or connected elongate probe and an elongate sleeve. Suction can be applied with a vacuum source operably connected to the proximal end region of the sleeve, whereby tissue of the surgical cavity is drawn against the surface of the sleeve. The probe includes one or more electrodes disposed at the probe's distal end region, for ablating tissue when the electrode(s) are activated to create an ablated margin of tissue at least partially surrounding the surgical cavity.

12 Claims, 12 Drawing Sheets

U.S. PATENT DOCUMENTS

| | | |
|---|---|---|
| 6,962,587 B2 | 11/2005 | Johnson et al. |
| 6,978,788 B2 | 12/2005 | Klimberg et al. |
| 7,025,765 B2 | 4/2006 | Balbierz et al. |
| 7,160,296 B2 | 1/2007 | Pearson et al. |
| 2002/0019640 A1* | 2/2002 | McGuckin, Jr. ............ 606/114 |
| 2002/0026188 A1 | 2/2002 | Balbierz et al. |
| 2002/0052545 A1 | 5/2002 | Klimberg et al. |
| 2003/0093008 A1 | 5/2003 | Van Bladel et al. |
| 2004/0010206 A1 | 1/2004 | Dubrul et al. |
| 2004/0147917 A1 | 7/2004 | Mueller, Jr. et al. |
| 2004/0193043 A1 | 9/2004 | Duchon et al. |
| 2005/0000525 A1 | 1/2005 | Klimberg et al. |
| 2005/0049586 A1 | 3/2005 | Daniel et al. |

OTHER PUBLICATIONS

Singletary, *American Surgeon*, 69(1):37-40, 2003, abstract only.

McManus et al., *American Surgeon*, 60(12):967-970, 1994, abstract only.

\* cited by examiner

CAVITY ABLATION APPARATUS AND METHOD

This application claims the benefit of priority from U.S. Provisional Application No. 60/665,407, filed Mar. 25, 2005, which is incorporated in its entirety herein by reference.

BACKGROUND

According to the American Cancer Society (ACS), about 9,420 new soft tissue cancers would be diagnosed in the United States in 2005. During 2005, 3,490 to Americans are expected to die of soft tissue cancers. The five-year survival rate for people with soft tissue sarcomas is around 90% if the cancer is found while it is small and before it has spread. In contrast, the five year survival rate is between 10% and 15% for sarcomas that have metastasized (www.cancer.org).

Surgery is the oldest form of treatment for cancer. Advances in surgical techniques have allowed surgeons to successfully operate on a growing number of patients. Today, less invasive operations are often done to remove tumors while preserving as much normal function as possible.

Complete local excision is generally considered adequate treatment for benign soft tissue tumors. Treatment of localized primary and recurrent sarcomas, however, may involve various treatment approaches, including surgery alone or surgery combined with radiation therapy or chemotherapy. With this method, the entire lesion is surgically removed. Many sarcomas appear to be well demarcated grossly. However, microscopically, there is usually a pseudocapsule with foci of infiltrating tumor. Removal of the tumor along this apparent plane may leave gross or microscopic sarcoma behind. Additionally, as many as 35% of patients develop local recurrence or distant metastases following surgical resection in addition to adjuvant therapy (www.emedicine.com).

Excisional biopsy may further be safely performed for small superficial tumors (approximately <5 cm in diameter) or those known to be benign.

According to the ACS, breast cancer is the most common cancer among women excluding non-melanoma skin cancers. In 2002, the American Cancer Society estimated there were 203,500 new invasive and 54,300 new cases of in situ breast cancer among U.S. women, resulting in the deaths of almost 40,000 women, ranking second among cancer deaths in women, behind lung cancer.

Over a lifetime, one in seven American women will experience breast cancer. Surgery, in one form or another, is still the primary approach to reduction or elimination of tumor mass in the breast. With earlier detection making it possible for breast cancer to be diagnosed while it is still localized (in situ), surgery (especially minimally invasive, breast conserving surgery) is increasingly a more effective tool in the treatment of this form of cancer.

It has been suggested to ablate a margin of a lumpectomy cavity with a cryogenic or radiofrequency device (Klimberg et al., U.S. Appl. 2005/0000525A1). The radiofrequency device is placed in the cavity and purse-string sutures are used to pull the tissue surrounding the device together. Electrodes are deployed from the distal end of the device and activated. However, the surgeon must estimate the position of the electrodes in the cavity to ablate the margins of the cavity. Further, the method is complicated as the surgeon must place the sutures and then the device must be held in place while the sutures are closed.

SUMMARY

In one aspect, the invention provides an apparatus for use in for ablating the margins of a cavity such as a surgical cavity formed in a tissue. In one embodiment, the apparatus includes an ablation device having an elongate probe having distal and proximal end regions and one or more electrodes disposed at the probe's distal end for ablating tissue when radiofrequency or microwave energy is applied to the electrodes. The apparatus includes at least one opening in the distal end region of the probe at which suction can be applied to the proximal end region of the apparatus to allow ablation of tissue drawn against the apparatus. Preferably, the one or more electrodes are aligned with the one or more openings, to allow deployment of the electrodes through the openings and ablation of tissue drawn against the openings when a vacuum is applied to the sleeve.

The apparatus may also include an insulating thermal barrier positioned around at least a portion of the distal end of the probe. The thermal barrier is preferably formed of a low thermal conductivity material. The apparatus may further include a sealing plate disposed at the proximal end region of the probe that is adapted to be pressed against a patient's surgical site, when the apparatus is inserted into the surgical cavity formed in the patent, to cover and seal the opening of the cavity.

In one embodiment, the apparatus further comprises at least one temperature sensor positioned at least one of (i) on the sealing plate for measuring the temperature at the surface of the surgical cavity, and (ii) on the sleeve for sensing temperature within the surgical cavity. In another embodiment, the apparatus includes at least one temperature sensor positioned on one or more of the thermal barrier surfaces. At least one thermal sensor may further be positioned between the thermal barrier and the sealing plate. At least one of the electrodes may also include a thermal sensor. It will be appreciated that all or some of the electrodes may include a thermal sensor. In a particular embodiment, each of alternating electrodes includes a thermal sensor.

The distal end of the probe may include a chamber that communicates with the openings and the proximal end region where the vacuum is applied. The apparatus may also include at least one vent positioned in the proximal portion of the probe that communicates with the distal end portion to provide air flow through the probe. Further, the apparatus may include a covering positioned around at least a portion of the distal-end of the probe and covering at least a portion of the opening.

In another aspect, the invention provides a method for ablating margins of a cavity such as a surgical cavity formed in a tissue. The method includes (a) inserting an elongate probe into the cavity, (b) applying suction at surface regions of the probe within the cavity, thereby to draw wall portions of the tissue into contact with the probe surface regions, wherein tissue margins in the surgical cavity surround the probe, and (c) while maintaining suction at the surface regions, ablating the tissue margins.

In one embodiment, step (c) includes (ci) introducing one or more electrodes into the tissue margins, and (cii) applying radiofrequency or microwave power to the electrodes until the margins have been ablated. In another embodiment, step (ci) includes deploying a plurality of electrodes into the margins at radially spaced intervals that, with the application of radiofrequency power to the electrodes in step (cii) define an ablation volume surrounding the probe and including the margins.

In one embodiment, the probe includes a plurality of radially spaced openings through which suction is applied to the surface region, and the electrodes are deployed through the openings in step (ci). In another embodiment, air flow is provided between the cavity through the distal end of the probe to and from a vent positioned in the probe. In another embodiment, after ablation of at least a portion of the cavity, suction is discontinued, the probe is repositioned within the cavity and the method repeated.

In yet another aspect, the invention provides an adapter for use with an ablation device of the type having (i) an elongate probe having distal and proximal end regions and (ii) one or more electrodes disposed at the probe's distal end region, for ablating tissue when power (such as radiofrequency or microwave power) is applied to the electrode(s). The adapter includes an elongate sleeve having distal and proximal end regions and is adapted to be placed over the distal end region of the probe. In one embodiment, the adapter includes a plurality of openings in the sleeve distal end region (i) at which a suction can be applied with a vacuum source operably connected to the proximal end region of the sleeve, and (ii) which are alignable with the one or more electrodes, to allow ablation of tissue drawn against the openings when the suction is applied to the sleeve, by application of power applied to the electrode(s).

In one embodiment, the adapter includes a thermally insulative barrier positioned around a distal portion of the sleeve. In a further embodiment, the adapter further includes a sealing plate disposed on the sleeve's distal end region that is adapted to be pressed against a patient's surgical site, when the probe is inserted into the surgical cavity formed in the patent, to cover and seal the opening of said cavity. The sealing plate may be axially slidable along the proximal end region of the sleeve. In one embodiment, the sealing plate is configured fit over a portion of a patient's breast. The adapter may further include means on the sleeve for limiting the axial movement of the sealing plate toward the sleeve's distal end. In another embodiment, the sleeve further includes at least one marker indicating the position of the sealing plate relative to the distal end of the probe.

In another embodiment, the adapter also includes an indicator on the sealing plate that indicates a sensed patient temperature. In one embodiment, the sealing plate includes at least one temperature sensor operatively connected to the indicator for sensing temperature at the surface of the surgical cavity. In another embodiment, the adapter further includes at least one temperature sensor on the sleeve and operatively connected to the indicator for sensing temperature within the surgical cavity. In yet another embodiment, at least one temperature sensor is positioned on at least one surface of the thermal barrier.

The adapter may include a multi-position lock at the sleeve proximal region for locking the position of the probe within the sleeve. In another embodiment, the adapter may include a lateral slide for aligning the probe within the sleeve.

The sleeve openings may have a microporous surface. In another embodiment, the adapter includes a semi-porous or porous sheath positioned over at least a portion of the openings.

In one embodiment, the sleeve, when placed over the probe's distal end region, forms a chamber therewith that communicates with the openings and with a port at the proximal region of the sleeve.

The adapter may also include an overflow relief valve positioned on the sealing plate.

The adapter may further include a valve and connection to the distal end portion of the sleeve to allow air flow through the adapter.

These and other features of the invention will become more fully apparent when the following detailed description is read in conjunction with the accompanying drawings.

BRIEF DESCRIPTION OF THE DRAWINGS

FIGS. 6A-6B show the probe in alternative positions using the locking mechanism of FIG. 5, FIG. 6C shows a linear slide mechanism;

DETAILED DESCRIPTION

I. Definitions

Figure 1A:
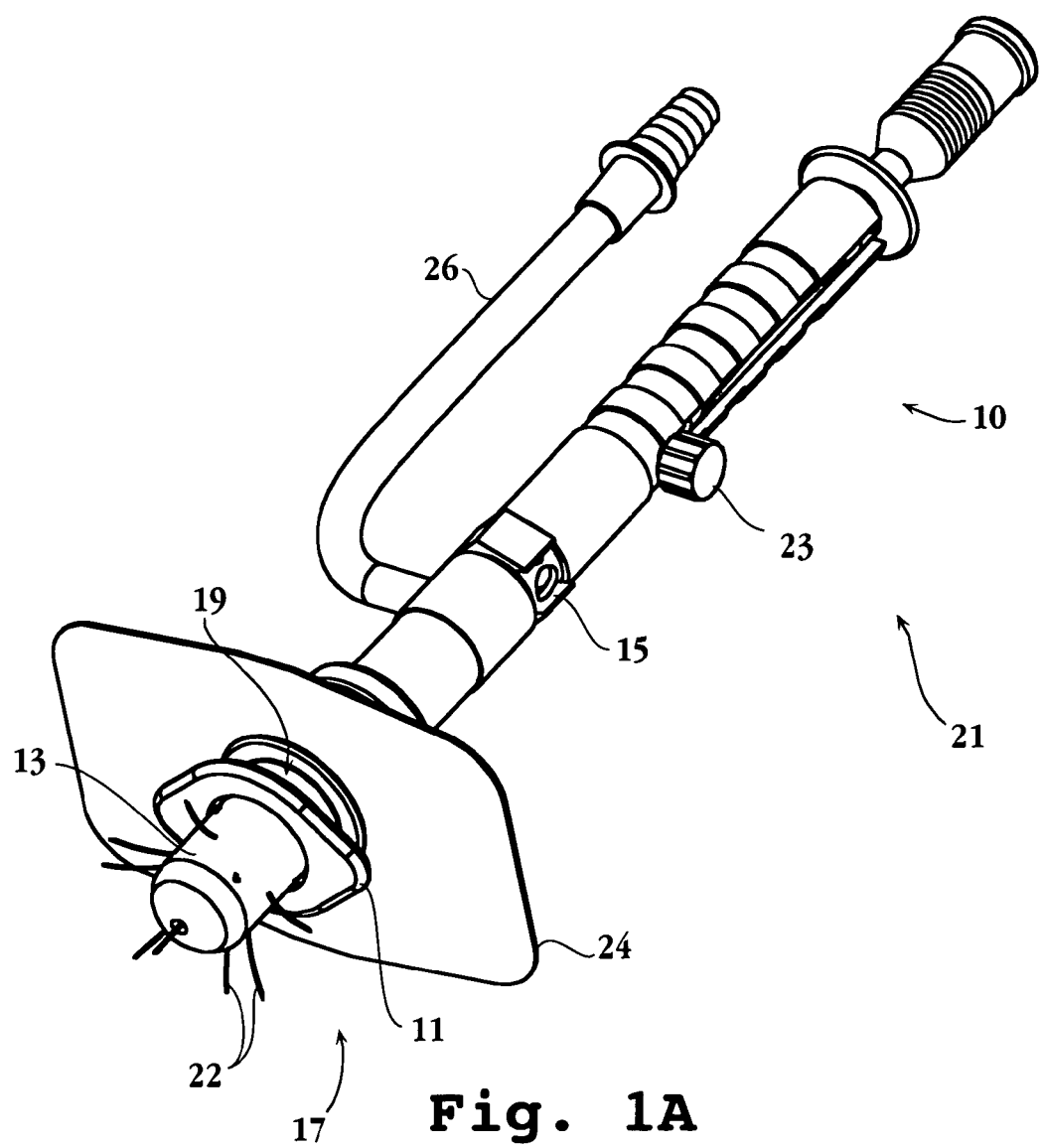
FIG. 1A is an illustration of an embodiment of the device for ablating the margins of a surgical cavity.

The terms below have the following meanings unless indicated otherwise.

"Radio Frequency" or "RF" refers to an electrical current that alternates the poles in the radio frequency range (extending from below 3 kHz to about 300 gigahertz.

"Soft tissue" refers to non-bone tissue.

A "tumor" refers to an abnormal lump or mass of tissue. Tumors can be benign (not cancerous) or malignant (cancerous).

"Cancer" as used herein refers to all types of cancer regardless of subset, therefore encompassing sarcoma, carcinoma, and other forms of cancer, invasive or in situ.

"Resection" refers to surgery to remove part or all of an organ or other structure.

"Distal end" with respect to an ablating instrument or introducer thereof, refers to the distal end or distal end region of the instrument, probe, or introducer thereof.

"Distal-end structure" or "distal-end member" refers to the ablating structure, e.g., needle, antenna, or electrode, carried at or deployable from the distal end of an ablating instrument or introducer thereof.

"Activating" or "activation", in the context of activating a distal end structure, e.g., electrode, refers to the application of a stimulus to the structure that is effective to ablate tumor tissue in contact with the structure. Such activation can include RF or microwave current applied to an electrode, current applied to a resistive heating element, ultrasound-generating current applied to an ultrasound generator or sonicator tip, a cryogenic fluid circulated through a circulation pathway in the probe, or an ablative fluid, e.g., ethanol or high salt, ejected from the end of a needle.

The term "vacuum" as used herein refers to a space at least partially exhausted of air using a vacuum source such as an air pump. Specifically, the term refers to a degree of rarefaction below atmospheric pressure.

"Suction" as used herein refers to reducing the air pressure using a source of suction such as an air or vacuum pump.

II. Apparatus

The cavity ablation system of the invention generally includes an instrument or device for use in ablating the margins of a cavity such as a surgical cavity. Resection of tumors may be performed in open surgery or percutaneously. In open resection, the surgeon typically makes an incision in the skin and excises the tumor and a margin of healthy tissue surrounding the tumor. The pathology of the excised tissue is reviewed using standard cytological techniques and the margin is determined to be negative, close or positive. Typically, a second surgery is required for close or negative margins. In the United States, nearly 40% of patients require a second surgery for close or positive margins on resection (Henry-Tillman, et al., *Semin. Surg. Oncol.,* 20(3):206-213, 2001). The goal of the resection is to obtain a negative margin, where no tumor cells are found, preferably within at least 1 cm of the edge of the resection. It will be appreciated that the device may further be used in any body cavity where ablation of the tissue surrounding the cavity is necessitated.

In one aspect, the present device provides for ablation of the tumor bed after excision to provide an ablated margin surrounding the tumor bed. Margins of 0.5 to 3.5 cm, inclusive, can be ablated around the tumor bed. In a preferred embodiment, a margin of at least about 1-2.5 cm is ablated at least partially surrounding the tumor bed. This ablated margin reduces the need for further surgery for resections with close or even positive margins. The ablated margin may further reduce the recurrence of tumor in the bed by providing an ablated margin at least partially surrounding the tumor bed even where the cytology results in a negative margin.

Generally, the device is suitable for use in ablating soft tissue tumor beds (a.k.a. surgical cavities) such as those resulting from breast lumpectomies, removal of tumors in the brain, or other surgical procedures in which a cavity is created. Depending upon the procedure, approximately 5 mm to 2 cm of tissue may be removed; however, the amount of tissue may be more or less depending on the size of the tumor, the procedure used for resection, the physician, among others. It will be appreciated that the device may be sized in accord with the size of the cavity. For example, the distal end of the device may be adjusted in length to accommodate the depth of the cavity. Further, multiple ablations may be used to ensure ablation of the cavity margins of various depth and/or width. It will further be appreciated the device may be used in a body cavity.

In one general embodiment, the device is placed at least partially in a tumor bed or other surgical cavity. Once positioned at target tissue site in the cavity, the apparatus can be configured to ablate tissue at that site as well as to create an ablated margin of tissue around the apparatus. The apparatus is formed of a probe or other elongate accessing member having a distal-end which is placed in the surgical cavity. The distal end of the probe includes a series of tubular sections operatively connected to a suction source surrounding at least a portion of the probe distal end. The suction sections include at least one opening on the outside, that is, the side facing the cavity wall. In a preferred embodiment, the at least one opening comprises a plurality of openings. The sections are connected at the proximal end to a source of suction, whereby when suction is applied, the tissue of the cavity wall is drawn adjacent the distal area of the probe. In this manner, the surgical cavity is "closed" against the probe. The probe further includes at least one activatable distal end region. In one exemplary embodiment, the distal end regions comprise one or more deployable electrodes or other activatable wires, antennas, or needles that can be deployed from the probe between the sections. The electrodes, when deployed, typically have a selected geometric configuration, such as a planar, or volume-forming configuration designed to ablate tumor tissue when activated. In another embodiment, the activatable distal end regions comprise one or more surface electrodes. In yet another embodiment, at least a portion of the probe distal end is activatable. The apparatus may further include a sealing member or plate disposed proximal to the distal region of the probe. As further discussed below with respect to the adapter, the plate is adapted to be pressed against a patient's surgical site to cover and preferably seal the opening of the cavity allowing for a more efficient vacuum to be applied the surgical cavity in order to draw at least a portion of the tissue to the probe and collapse the open spaces within the cavity, whereby the peripheral tissue is brought into contact with the electrodes when deployed. The plate may be formed of a transparent material to allow for visual inspection of the cavity surface. In another embodiment, the apparatus may include a thermally insulative barrier or skirt surrounding a portion of the distal end of the probe. This barrier serves to limit the thermal effect of the activatable regions to the area distal to the barrier, thus to define the ablation area and prevent burns to the skin. The barrier may be fixed to the distal end of the probe or be slidably attached to the probe. Where the device includes a sleeve, discussed further below, the barrier may be fixed to the sleeve or movably positioned around the sleeve. The apparatus may also include an intake or vent in the probe that communicates with the distal end of the probe to allow for at least a small amount of air flow to and from the cavity. In this manner, residual steam may be carried away from the ablation area.

In another embodiment, the apparatus makes use of commercially available ablation devices. In this embodiment, the device generally includes an elongate probe and a tubular sleeve, where the probe is positioned at least partially in the sleeve. The probe includes at least one distal-end structure adapted to be inserted into the walls of the cavity, where the structure is activatable to ablate the walls of the cavity and create an ablated margin of tissue surrounding the cavity. It will be appreciated that the device includes connecting structure for connecting the distal-end structure to an activating device. The assembly, and particularly the suction instrument, of the invention will now be described with reference to the figures.

For convenience, similar element numbering is retained in FIGS. 1-9 to identify like structural features. For example, the sealing plate is numbered 24 in FIG. 1A, 224 in FIG. 2A, 424 in FIG. 4, etc.

Figure 1B:
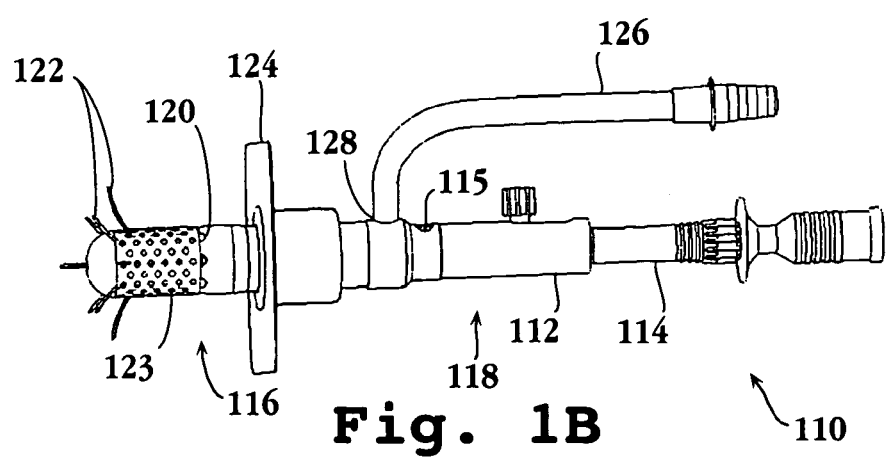
FIG. 1B is an illustration of another embodiment of the device for ablating the margins of a surgical cavity.

In the embodiment seen in FIG. 1B, the apparatus 110 includes an ablation device 114 comprising an elongate probe having a distal region and a proximal region. In one embodiment, the probe includes at least one or more electrodes or antennas 122 deployable from the distal end of the probe for ablating tissue when activated. In one exemplary embodiment, a plurality of electrodes is deployable from the probe distal end. It will be appreciated the electrodes may be deployed radially or asymmetrically from the probe depending on the location of the tissue to be treated or critical structures to be avoided. In another embodiment, the probe includes at least one activatable end region carried on the distal region of the probe. It will be appreciated that the electrodes or activatable end regions may be activated by application of RF or microwave current applied to a conductive material such as an electrode or an antenna, current may be applied to a resistive heating element (tip or electrode). In other embodiments, ultrasound-generating current may be applied to an ultrasound generator or sonicator tip, a cryogenic fluid may circulated through a circulation pathway in a tip, or an ablative fluid, e.g., ethanol or high salt, may be ejected from the end of a needle tip. In a preferred embodiment, the activatable end regions are RF or microwave electrodes or antennas. It will be appreciated that the elongate probe may further utilize a combination of activating methods.

The at least one electrode may be two or more electrodes for bipolar electrode configurations and/or an array of electrodes (either bipolar or monopolar). The electrodes can be operated in monopolar or bipolar modes, and may be capable of switching between the two modes. The electrodes can be coupled to the power supply and/or a ground pad electrode, in monopolar mode, via an insulated wire which can be a guidewire. The coupling can also be made via a coaxial cable, thereby allowing for coupling of one or both electrodes to the power supply as a ground pad electrode. In embodiments, the electrodes are coupled to the power supply such that power may be independently applied to each electrode. The electrodes may be independently coupled to the power supply where the power supply has independent channels, or the electrodes may be coupled to a multiplexer that controls power to each of the electrodes separately.

The electrodes can be made of a variety of conductive materials, both metallic and non-metallic. Suitable materials for the electrode include, in non-limiting embodiments, steel such as 304 stainless steel of hypodermic quality, platinum, gold, silver and alloys and combinations thereof. Also, the electrodes can be made of conductive solid or hollow straight wires of various shapes such as round, flat, triangular, rectangular, hexagonal, elliptical, and the like. In a specific embodiment all or portions of electrodes can be made of a shaped memory metal, such as NiTi, commercially available from Raychem Corporation, Menlo Park, Calif. A radiopaque marker can be coated on the electrodes for visualization purposes.

The electrodes can be coupled to the probe using soldering, brazing, welding, crimping, adhesive bonding and other joining methods known in the medical device arts.

In one embodiment, the apparatus further comprises an elongate sleeve 112 integral with or carried on the distal end region of the probe. The sleeve preferably comprises an elongate tubular barrel having a proximal region 118 and a distal region 116. The sleeve is preferably open at the proximal end for receiving and engaging at least part of the distal end region of the probe. The sleeve includes at least one opening 120 in the distal end region. In a preferred embodiment, the sleeve includes a plurality of openings in the distal end region. Where the apparatus includes deployable electrodes or antennas, the electrodes are aligned with the openings such that the electrodes are deployable through the openings. In one embodiment, the sleeve partially houses the probe, forming therewith, a chamber that communicates with the openings and the proximal region of the sleeve. The sleeve and/or the probe may include a marker system for connecting the sleeve and the probe such that the electrodes are aligned with the openings and deploy through the openings. As seen in FIG. 1A, the probe may include a knob or slide 23 for deployment of the electrodes 22. In the embodiment shown, the electrodes are deployed when the knob is moved towards the distal end of the probe. As the knob is moved toward the proximal end of the probe, the electrodes are retracted within the device.

At least a portion of the sleeve and/or probe can be made from a variety of resilient polymers including elastomers, polyesters, polyimides, fluoropolymers and the like. The sleeve can be configured to be both electrically and/or thermally insulative or can be electrically and/or thermally conductive using conductive polymers known in the art. An example of a conductive polymer includes Durethane C manufactured by the Mearthane Products Corporation (Cranston, R.I.). The sleeve can further be formed of a conductive material such as stainless steel, nickel, platinum, and/or aluminum. It will be appreciated that different portions of the sleeve and/or probe may be made of different materials.

Figure 3:
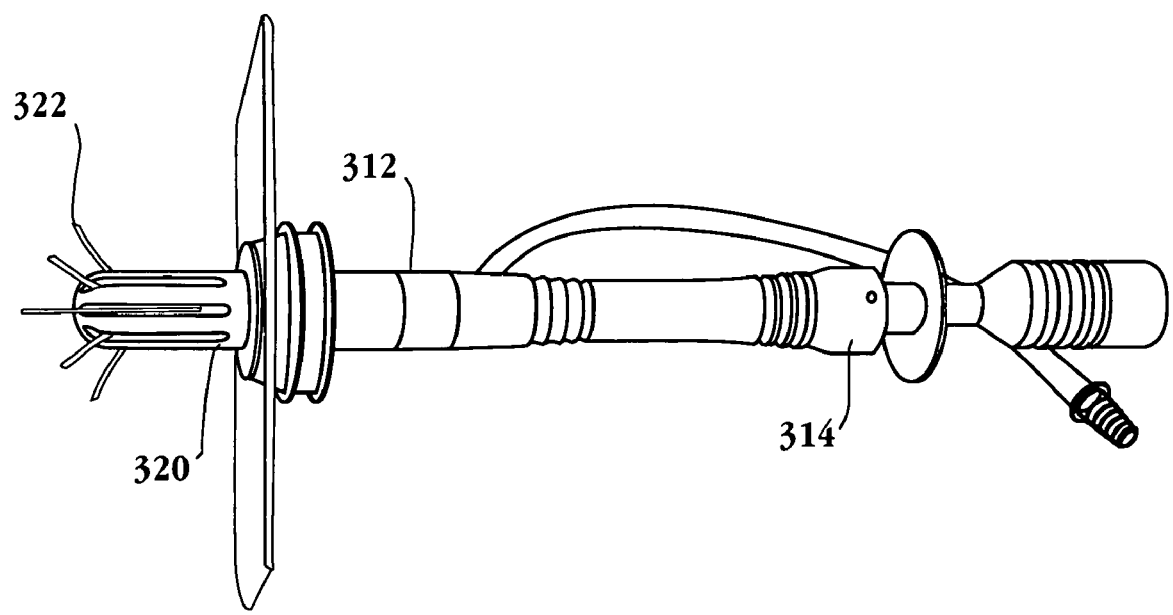
FIG. 3 is a scanned image of an embodiment of a suction ablation device.

The sleeve can be made to any suitable shape and size depending on the length of the ablation device and/or the depth/width of the cavity. Suitable shapes include, but are not limited to, cylindrical, ellipsoid, football shaped, etc. In one preferred embodiment, the sleeve is an elongate, tubular barrel. The sleeve preferably includes a cylindrical distal portion adapted to at least partially house and engage the distal region of the ablation device. As seen in FIG. 3, the sleeve 312 preferably includes a cylindrical distal portion including at least one opening 320 configured to receive at least one electrode 322 of the ablation device 314. In a preferred embodiment, the sleeve has a non-tissue piercing distal end.

The opening(s) may be microporous or include a covering to prevent tissue from clogging the opening(s). In another embodiment, the openings may include a plurality of openings sized to prevent clogging from the tissue. In yet another embodiment, the openings include a tissue filter 13 positioned on the outer or inner surface of the openings or covering to prevent clogging of the openings with tissue. In one embodiment, the filter is a perforated, meshed, or weaved membrane sized to allow the electrodes 22 to deploy therethrough. In another embodiment, the opening may be covered by a porous material such as a plastic or gel that the electrodes pierce when deployed through the openings. In yet another embodiment, the openings may be covered by a mesh or screen where the electrodes deploy through the mesh screen. The mesh may be a spiral mesh. The mesh screen may be formed of any suitable material including, as non-limiting examples, metals such as stainless steel or brass, polyester, nylon, and fiberglass. In a preferred embodiment, the mesh is formed from nylon monofilament fiber. The mesh may be any suitable mesh including, but not limited to, a welded, monofilament, or perforated mesh.

In another embodiment, the apparatus further includes a tubular sheath or covering 123 surrounding at least a portion of the distal region of the sleeve and at least partially positioned over the at least one opening. The sheath may further be affixed to the sleeve. The sheath is preferably a semiporous or porous membrane or mesh. The sheath is preferably low profile and sized to prevent interference with the movement of the apparatus or deployment of the electrodes. The sheath may be formed of any suitable material that allows penetration of the electrodes. Preferably, the material is semiporous or porous. In another embodiment, the material is made porous by mechanical means such as stamping or piercing. Exemplary materials include plastics and polymers such as silicon, Dacron™, and ethylene vinyl acetate (EVA).

As shown in FIG. 1A, the apparatus 10 may further include a thermally insulative barrier, shield, or heat skirt 11 positioned around the distal end portion 17 of the probe. The barrier is preferably positioned distal to the plate 24. This barrier serves to limit the thermal effect of the activatable region. In this manner, the ablation area may be contained and/or skin burns minimized. The barrier may be formed of any suitable low thermal conductivity material. Non-limiting examples include ceramic, foam, and plastics such as polyetherimide (Ultem). The barrier may be any suitable shape as needed for the cavity such as elliptical, oval, circular, etc. In another embodiment, the barrier includes an internal air or liquid chamber to allow air flow through the barrier to provide cooling to protect critical structures such as the skin. In yet another embodiment, the barrier is configured to allow for circulation of air and/or a liquid for cooling. In a non-limiting example, the barrier includes an internal spiral chamber with at least one intake opening whereby air may be pumped into or drawn into the chamber to circulate therethrough. The barrier may also include an opening for the air and/or liquid to exit. In the embodiment where the probe includes a vent, the air or liquid may be drawn out of the cavity through the vent. In another embodiment, the air or liquid is recirculated through the barrier and/or a cooling system. Also shown are the proximal portion of the probe 21 and the tubing connector 26 for connection to the suction source.

In one embodiment, the sleeve is affixed to the probe through any suitable means such as a clip, lock, or other fastener. In the embodiment seen in FIG. 5, the fixture is a linear slot 535 in the proximal portion of the sleeve 512, whereby at least a portion of the probe 514 is positioned in the slot to provide alignment of the electrodes with the openings when the electrodes (622 in FIGS. 6A-6B) are deployed. At least a portion of the probe is slidably positioned in the slot, where the maximum proximal and distal axial movement of the probe within the sleeve is determined by the length of the slot. In another embodiment, as seen in FIGS. 6A-6B, the fixture is a lock positioned in the sleeve 612 including multiple slot positions 634, 636 for receiving at least a portion of the probe 614. In yet another embodiment, not shown, the sleeve is not affixed to the probe and is, instead, axially slidable along the distal region of the probe. In a further embodiment, the sleeve is integral with or fixed to the probe.

In a preferred embodiment, suction can be applied at the opening(s) by applying a vacuum to the proximal end region of the sleeve to draw tissue adjacent or against the sleeve or collapse the cavity against the sleeve allowing ablation of the tissue drawn against or adjacent the surface of the sleeve when a vacuum is applied to the opening(s). In one embodiment, the sleeve includes at least one port 128 for connection to a source of suction. Port 128 may be, but is not limited to, a luer fitting, a valve (one-way, two-way), a toughy-bourst connector, a swage fitting, and other adaptors and medical fittings known in the art. The connection is also referred to herein as connecting structure, and may include tubing, fittings, couplings, or any fastening suitable for providing suction therethrough from a suction source to the apparatus. The suction source may be connected to the sleeve through any suitable connector as exemplified by standard ¼ inch medical suction tubing and fittings 126. The suction source may be the standard suction available in the operating room and may be coupled to the device using a buffer. In other embodiments, suction can be applied from a conventional vacuum generator such as a vacuum pump, a venture vacuum generator powered by pressurized air or water supply, or an external vacuum unit. It will further be appreciated that any suitable suction source may be used with the device including, but not limited to, a vacuum pump or the standard surgery vacuum. The amount of suction applied to the apparatus is non-limiting as long as the suction is sufficient to draw the walls of the cavity adjacent the sleeve. Typically, the suction is provided at a negative pressure of about 0 to about 736 mm Hg. It will be appreciated that the settings for vacuum pressure may vary depending on the tissue type, size of the cavity, and the age, health, and body type of the patient. In one embodiment, the suction is suitable to retain the apparatus substantially vertical to the surface of the treatment tissue.

In another embodiment, the distalmost end of the sleeve or probe is at least partially open forming a nozzle at the distal end of the probe. When suction is applied to the apparatus, the tissue is drawn into the nozzle. In this embodiment, electrodes may be positioned at the interior of the nozzle or the distal end of the probe may be conductive for ablation of the tissue drawn into the nozzle. It will be appreciated that the distal end of the probe may be concave or tubular shaped to allow for drawing the tissue therein. It will be appreciated that this embodiment is particularly useful for cysts, polyps as well as any other tissue that may be isolated in this manner for ablation.

The apparatus may include a seal disposed between the sleeve and the probe to prevent flow of air between the sleeve and the probe. Any suitable sealing member may be used including, but not limited to, an o-ring, gasket, or flange.

The apparatus may further include a vacuum control valve or port 15, 115 for regulation of the amount of vacuum obtained at the opening(s). In one embodiment, the valve is an on/off valve such that when the valve is in the open position, air is drawn from the valve opening on the sleeve whereby little or neglible vacuum achieved at the opening(s) in the sleeve distal region. When the valve is in the closed position, the vacuum is achieved at the opening(s) in the sleeve distal region. In another embodiment, the apparatus may include a vacuum control, not shown, as known in the art to regulate the amount of vacuum achieved. In another embodiment, the apparatus includes an overflow relief valve whereby air is allowed to enter the cavity when an excess of suction is applied to the cavity. The vacuum control may be manually or automatically operated.

The apparatus may further include a sealing member or plate 124 disposed at the distal region 116 of the sleeve. The plate is adapted to be pressed against a patient's surgical site when the probe is inserted into the surgical cavity formed in the patent, to cover and seal the opening of said cavity. The covering allows for a more efficient vacuum to be applied to the surgical cavity to draw the tissue to the sleeve. It will be appreciated that the size of the plate is non-limiting as long as the plate is sized to at least cover the opening of the surgical cavity. It will be appreciated that the plate may be adjusted or cut down in accord with the size of the surgical opening. The plate can be constructed from rigid polymers such as polycarbonate or ABS or resilient polymers including Pebax®, polyurethane, silicones HDPE, LDPE, polyesters and combinations thereof. In a preferred embodiment, the plate is formed of a pliable or compliant material. It will be appreciated that the sealing plate may be formed of a transparent, semi-transparent, or opaque material. Where the plate is formed of a transparent material, the cavity may be monitored for wrinkles, dimples, pockets, etc., which can indicate an air pocket, and/or incorrect or incomplete suction of the tissue to the probe. The sealing plate may be made in any suitable shape for covering the cavity opening and contacting the tissue surface, including, but not limited to circular, oval, elliptical, rectangular, and square. Where the plate is conformable, the plate may be any suitable thickness that allows the plate to conform to the tissue surface, yet is resilient enough to resist being drawn into the cavity. In an exemplary embodiment, the plate is formed of silicone having a thickness of about 0.076 inches. In one embodiment, at least one face of the sealing plate includes a conformable surface that conforms or bends to the shape of the tissue surface. This can be accomplished by constructing all or a portion of the plate from resilient polymers including but not limited to elastomers such as silicone and polyurethane and polymers thereof as well as foam rubber. The plate can be fabricated from such materials using injection molding or mandrel dip coating methods known in the art. One or both surfaces of the plate may further be coated with an agent that improves contact with the skin and/or assists in the formation of the seal. In another embodiment, the plate may be treated to impart desired properties to the plate. An exemplary coating is a slippery or lubricous agent coated on the tissue contact surface of the plate to prevent the skin adhering to the plate. A non-limiting example is a plate that is plasma treated on the tissue contact surface to provide a lubricous surface. A preferred example is a silicone plate that is plasma treated on the tissue contact surface. The sealing plate may be a solid plate, include one or more plate sections, or include baffles or passages to allow air flow between two or more plates. In this manner, the tissue surface may be cooled to prevent or reduce the occurrence of burns. The plate may further include a marker 252 or markings to externally indicate the extent of the ablation margin. For example, the plate may have an indicator to show the extent of ablation based on the deployment of the electrodes.

In one embodiment, the sealing plate is axially slidable along the proximal region of the sleeve. It will be appreciated that shallow ablations (generally less than 1 cm) may cause burning or blistering of the skin. Accordingly, in one embodiment, the apparatus includes means on the sleeve for limiting the axial movement of the sealing plate toward the sleeve's distal end to prevent skin burns. Exemplary means for limiting axial movement include a stop or resistive gradient on the sleeve or the plate. In another embodiment, markers 250 can be disposed along the sleeve to facilitate identification of the location of the probe distal end within the sleeve. In this manner, the surgeon can position the sealing plate to allow at least about 1 cm between the sealing plate and the distal end of the probe within the sleeve.

In another embodiment, the sealing plate comprises at least one port for connection to the suction source, not shown. In this embodiment, the vacuum in the cavity is created by applying suction to the sealing plate port. It will be appreciated the suction may be applied at the sealing plate port alone or in conjunction with applying suction at the at least one opening in the sleeve.

The sealing plate may further be formed of a conductive material, where the plate acts as a ground pad electrode. In this embodiment, the plate may be directly connected to the power source, or may be connected through the apparatus. In this embodiment, the sealing plate should be of a sufficient size to provide adequate dissipation of current to prevent burns. In another embodiment, the sealing plate may be hollow or comprise an area for conductive air flow to dissipate heat. The hollow plate may also be connected to the suction source to facilitate and enhance heat dissipation by conductive air flow.

Figure 9:
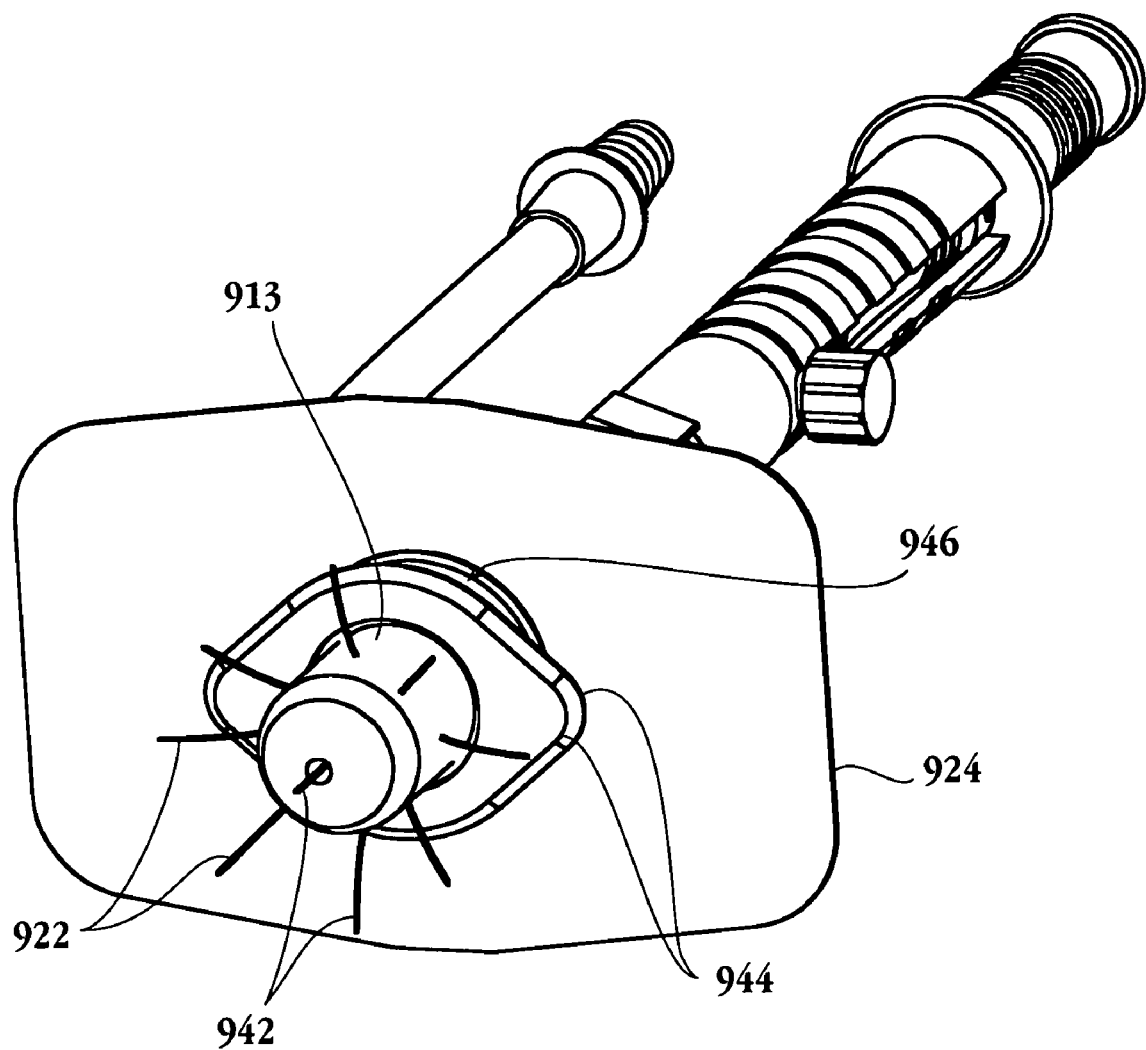
FIG. 9 is an illustration of the positioning of the probe showing locations of the thermal sensors.

As shown in FIG. 9, the apparatus may further comprise at least one temperature sensor positioned at least one of (i) on the sealing plate 924 for measuring the temperature at the surface of the surgical cavity, (ii) on the sleeve 913 for sensing temperature within the surgical cavity, and/or (iii) on one or more surfaces of the thermal barrier 944. Where the sensor(s) is positioned on the thermal barrier, it will be appreciated that sensor(s) positioned on the distal side of the barrier or the area of the probe or sleeve distal to the barrier (see 19 in FIG. 1A), where used, will approximately measure the temperature of the tissue being ablated. Sensor(s) positioned on the proximal side of the barrier or the proximal portion of the probe or sleeve will approximately measure the temperature of the tissue cavity that is not ablated. In this manner, skin burns can be minimized and/or prevented. The sensor may be any suitable thermal sensor. The apparatus may further include a temperature indicator positioned on the sealing plate. This indicator may include thermotropic liquid crystals that change position according to changes in temperature. The liquid crystals can be calibrated as a visual indication of a desired temperature or end point for the ablation. In another embodiment, at least one sensor is positioned on the sealing plate operatively connected to the indicator for sensing and indicating temperature at the surface of the surgical cavity. In another embodiment, the apparatus includes a temperature sensor positioned on the sleeve and operatively connected to the indicator for sensing temperature within the surgical cavity. At least one of the electrodes 922 may also include a thermal sensor 942. It will be appreciated that all or some of the electrodes may include a thermal sensor. In a particular embodiment, alternating electrodes include a thermal sensor. Thermal sensors can include thermistors, thermocouples, resistive wires, optical sensors and the like. A suitable thermal sensor includes a T type thermocouple with copper constantene, J type, E type, K type, fiber optics, resistive wires, thermocouple IR detectors, and the like. It will be appreciated that the control of power to the electrodes may be adjusted or controlled based on feedback from the at least one thermal sensor. The feedback may be a closed-loop whereby a feedback signal is received at a control or the energy source, which then regulates the amount of energy or current delivered to electrodes. In another embodiment, the power may be manually regulated based on feedback from the at least one thermal sensor.

Figure 2A:
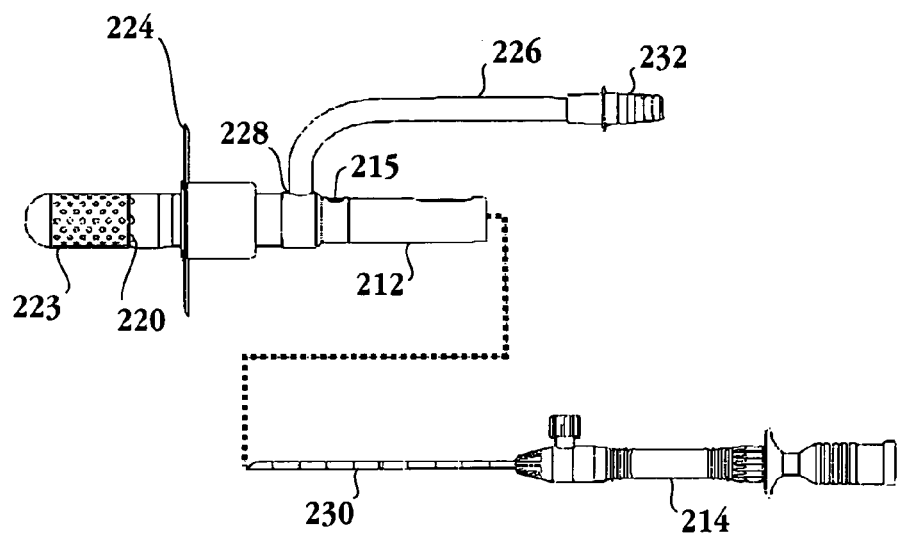
FIG. 2A is an illustration of the device of FIG. 1B showing the sleeve detached from the probe.
Figure 2B:
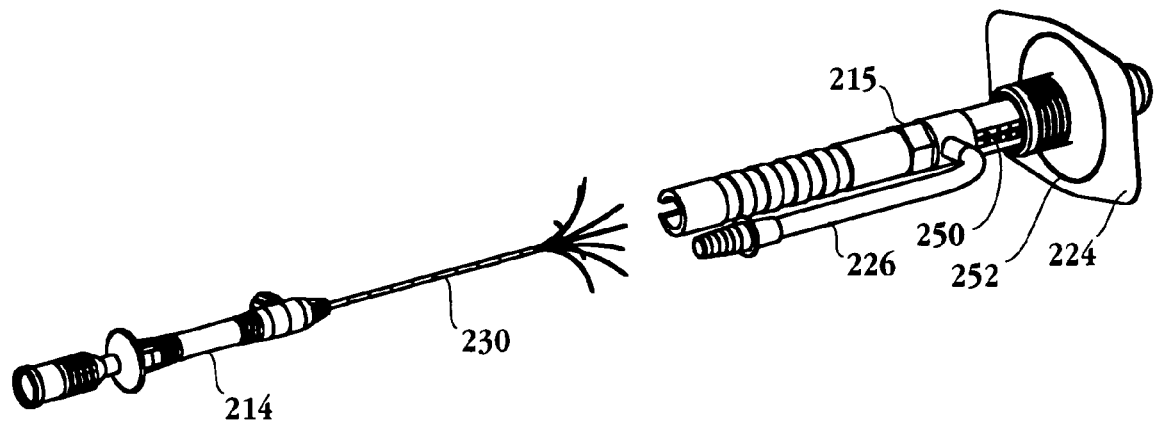
FIG. 2B is an illustration of the device of FIG. 1A showing a modular aspect with the sleeve detached from the probe.

As seen in FIGS. 2A-2B, the sleeve may be an adapter 212 for use with an ablation device 214 of the type having (i) an elongate probe having a distal region 230 and a proximal end region and (ii) one or more electrodes disposed at the probe's distal end region, for ablating tissue when radiofrequency or microwave power is applied to the electrode(s). An exemplary ablation device is the Starburst XL™ (RITA Medical Systems, Inc., Mountain View, Calif.).

A variety of activation devices, including energy-delivery devices such as power sources, can be utilized by embodiments of the invention. Specific energy delivery devices and power sources that can be employed in one or more embodiments include, but are not limited to, the following: (i) a microwave power source adapted to be coupled to a microwave antenna distal end tip, providing microwave energy in the frequency range from about 915 MHz to about 2.45 GHz (ii) a radio-frequency (RF) power source adapted to be coupled to a distal end electrode, (iii) a reservoir containing heated fluid adapted to be coupled to a catheter with a closed or at least partially open lumen configured to receive the heated fluid, (iv) a reservoir of a cooled fluid adapted to be coupled to a catheter with a closed or at least partially open lumen configured to receive the cooled fluid, e.g., a cryogenic fluid, (v) a resistive heating source adapted to be coupled to a conductive wire distal-end structure, (vi) an ultrasound power source adapted to be coupled to an ultrasound emitter tip, wherein the ultrasound power source produces ultrasound energy in the range of about 300 kHz to about 3 GHz, and (vii) combinations thereof. In a preferred embodiment, the power source is a RF energy source such as the 1500X RF generator (RITA Medical Systems, Inc. (Mountain View, Calif.), which delivers 1-250 W at 460 kHz. The 1500X RF generator provides temperature control of 15° C.-125° C.±3° C.

In one preferred embodiment, the energy delivery device is an RF power supply that provides RF current to one or more RF electrodes. In embodiments, the RF power supply delivers electromagnetic energy in the range from 5 to 200 watts to the electrodes at about 450 V although it will be appreciated that wider ranges of energy delivery levels may be possible with different power supplies as well as with different configurations. The electrodes are coupled to the energy source either directly to each electrode, or indirectly using a collet, sleeve, connector, cable and the like which couples one or more electrodes to energy source. Delivered energies can be in the range of 1 to 100,000 joules, with embodiments having ranges of approximately 100 to 50,000 joules, 100 to 5000 joules, and 100 to 1000 joules. Lower amounts of energy can be delivered for the ablation of smaller structures such as nerves and small tumors as well as higher amounts of energy for larger tumors. Also delivered energies can be modified (by virtue of the signal modulation and frequency) to ablate or coagulate blood vessels vascularizing the tumor. This provides for a higher degree of assurance of ablation of the blood supply of the tumor.

The adapter includes at least one, or a plurality of, opening(s) 220 in the distal end region of the adapter. In operation, the electrodes of the ablation device are aligned with the openings such that the electrodes deploy through the openings into the target tissue. The adapter may comprise a tubular sheath 223 surrounding the distal region of the sleeve and at least partially positioned over the at least one opening. The sleeve may include a port or connector 228 for connection to a source of suction. The suction source may be connected to the port through any suitable connection such as tubing 226 and fittings 232. The port may further be connected to the distal region of the sleeve through an internal passageway. The sleeve may further include a vacuum control valve or port 215 as further described above.

In one embodiment, the adapter includes a sealing member or plate 224 disposed on the distal region of the sleeve. The sealing plate may comprise a planar cover and a ring slidable around the tubular distal region of the sleeve. In a preferred embodiment, the sealing member is positioned distal of port 228. The planar cover may be pliable, rigid or semi-rigid. The planar cover may further include at least one face with a convex, concave, flat, or substantially flat surface. As noted above, the cover and/or the ring of the sealing plate are constructed from rigid polymers such as polycarbonate or ABS or resilient or flexible polymers including Pebax®, polyurethane, silicones HDPE, LDPE, polyesters and combinations thereof. The sealing member may be integral with or connected to the sleeve. It will be appreciated the sealing member may further include a port, not shown, for connection to a suction source.

Figure 7:
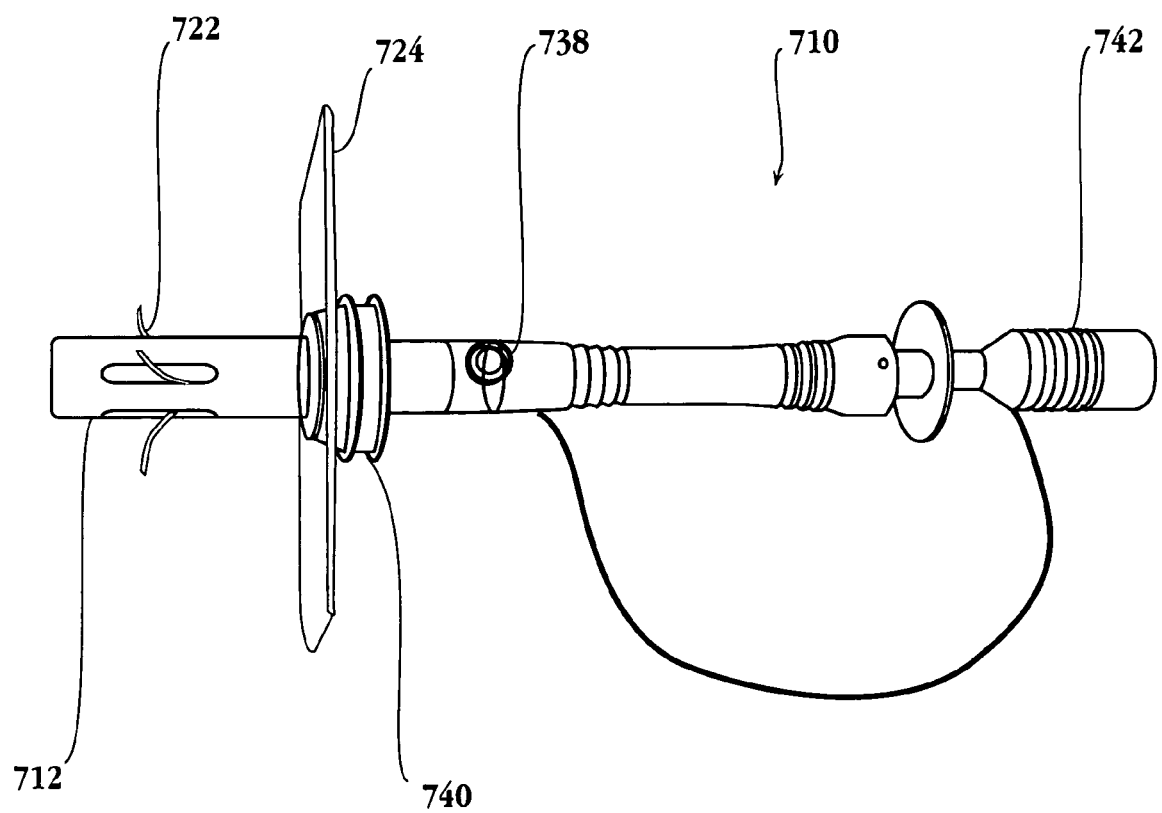
FIG. 7 is a scanned image an embodiment of the device for ablating the margins of a surgical cavity.

As seen in FIG. 7, in another embodiment, the apparatus 710 includes an activatable distal end 712 formed of a conductive material. The apparatus may include one or more deployable electrodes or non-conductive probes for thermal sensing 722. The distal end includes one or more openings operatively connected to a suction port 738. When suction is applied, the cavity walls are drawn to the distal end of the apparatus. The distal end is activated to ablate a margin of tissue surrounding the distal end forming an ablated margin. The apparatus may further include a sealing plate 724 to cover and/or seal the opening of the surgical cavity. The sealing plate may be connected to the apparatus by a flexible baffle 740 such that the plate is pressed securely against the skin surface. In one embodiment, an actuator 742 is used to retract and deploy the electrodes or non-conductive probes.

III. Method of Using Cavity Ablation Device

The following discussion pertains particularly to the use of an RF energy source and treatment/ablation apparatus. For purposes of this discussion, the activatable distal ends are referred to as RF electrodes/antennas and the energy source is an RF energy source. However it will be appreciated that all other energy delivery devices and sources discussed herein are equally applicable. It will be appreciated that any RF generator capable of delivering power in the required range is suitable for use in the present method including, but not limited to, the EPT-1000 TC™ RF generator (Boston Scientific, Natick, Mass.), the S-350RF generator (Electropulse, Russia), and the Cool-Tip™ Generator (Valley Lab, Boulder, Colo.).

In another aspect, the invention includes a method of ablating margins of a surgical cavity formed in a tissue. The surgical cavity is generally a tumor bed where a tumor and margin of healthy tissue have been excised by the treating worker, e.g., physician. The surgical cavity is generally a tubular, cylindrical, or "football" shaped hole with at least one opening at the skin. The method includes ablating the vertical walls and/or the bottom of the cavity.

Figure 4:
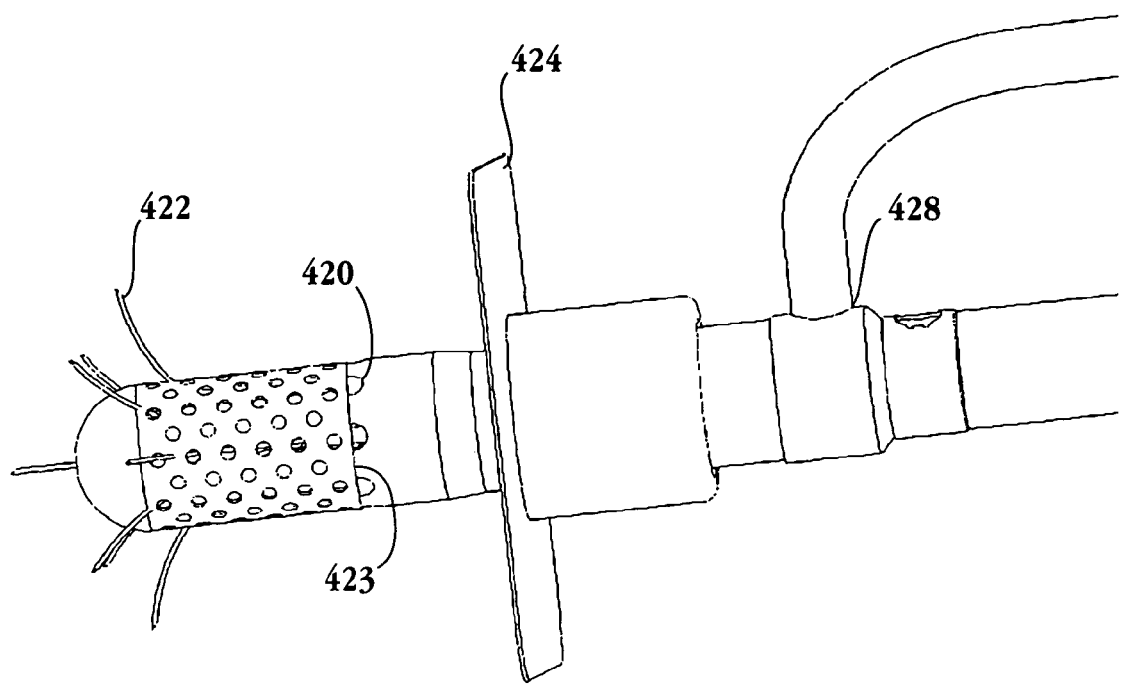
FIG. 4 is a detailed view of the apparatus distal portion of the device of FIG. 1A with a detailed view of the sleeve distal area.

Once a tumor lesion is removed, the physician inserts the apparatus at least partially into the surgical cavity. The apparatus is preferably manipulated to place the tip of the instrument at or near the bottom of the cavity. If the apparatus has one or more deployable electrodes, the apparatus is usually inserted into the cavity with the electrodes in a retracted state. The position of the apparatus with respect to the target area can be confirmed by conventional imaging techniques, as further described below. As seen in FIG. 4, in one embodiment, a sealing plate 424 or adjustable cover may be axially adjusted along the sleeve to position the plate against the tissue surface thereby to seal the surgical cavity and assist creating the vacuum in the cavity. When suction is applied, the tumor bed collapses against the surface of the apparatus.

A suction source connected to the apparatus at port 428 is used to apply suction at distal surface regions of the apparatus and create a vacuum in the cavity, thereby to draw at least a portion of the cavity wall into contact with the apparatus. Once the apparatus is so positioned, the electrode(s) 422 are deployed through the openings 420 at the sleeve distal region and piercing the sheath 423. As indicated above, the electrodes, and particularly deployable electrodes, can be shaped such that in the deployed state they form a desired geometric configuration. In one embodiment, the electrodes are independently deployed from the probe distal end. It will be appreciated that all or a portion of the electrodes may be deployed with different shapes or to different lengths. It will further be appreciated that not all of the electrodes may be deployed, especially where an asymmetric ablation is desired. The electrodes may further be deployed a variable distance from the sleeve to create the appropriate margin. The electrodes may be deployed to a desired depth in the tissue, or may be deployed step-wise to a maximum depth while delivering power. Specific margins to be ablated include 0.5 cm, 1 cm, 1.5 cm, or more. In one embodiment, a plurality of electrodes are deployed into the cavity walls at radially spaced intervals that, with activation of the electrodes define an ablation volume surrounding the apparatus and form the ablated margin.

Preferably, while suction is maintained the electrodes are activated to ablate surrounding tissue and create an ablated margin. In the preferred embodiment, this step involves applying an RF current to one or more electrode structures carried on or deployed from the probe distal region. Power and duration levels for application of RF current are detailed above. Typically, ablation is carried out up to a target temperature and held at the target temperature to allow heat dissipation through to the tissue surrounding the electrode surface. The target may be a selected temperature, e.g., 100° C. or greater, a selected temperature over a give time period, e.g., 45° C. to 100° C. for a period or 5-20 minutes, or a rapid increase in impedance. It will be appreciated that the ablation endpoint may be adjusted based the tissue ablated, the size of the cavity, etc. A typical ablation in breast tissue is ablating the tissue at 100° C. for 15 minutes. A typical endpoint is a thermal dose or time at a specified temperature. Both the temperature and the time may be dependent on the tissue being ablated.

Figure 5:
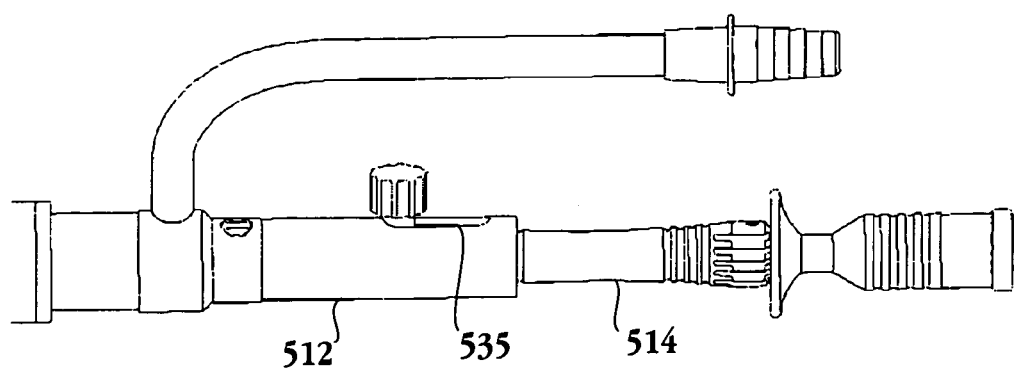
FIG. 5 is an illustration of a detailed view of a locking mechanism.
Figure 6A:
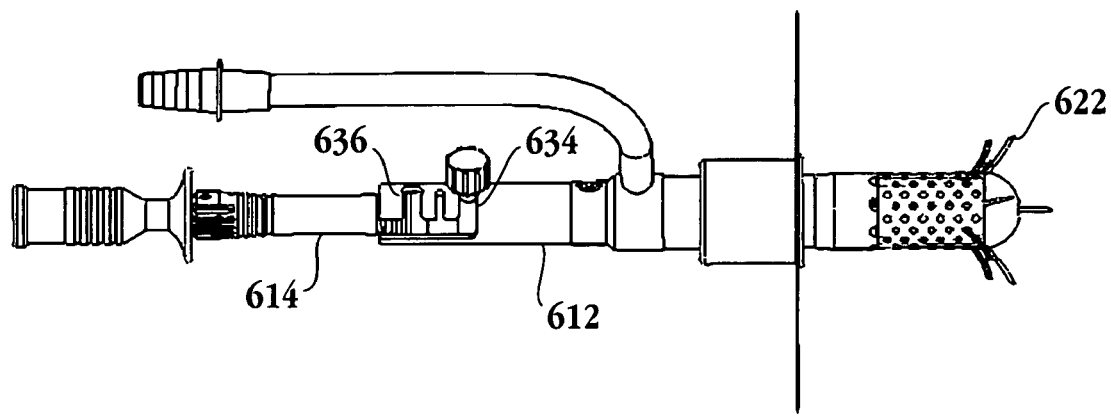
FIGS. 6A-6C are illustrations of the positioning of the probe within the sleeve.
Figure 6B:
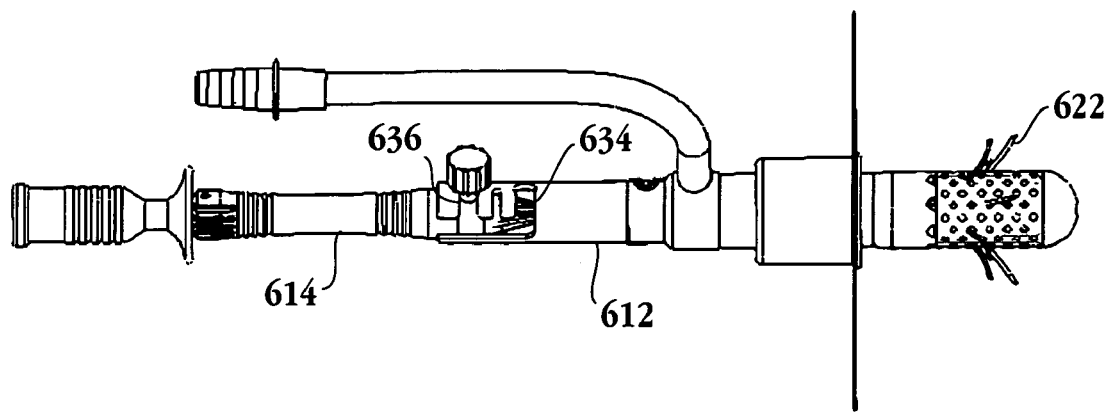
Figure 6C:
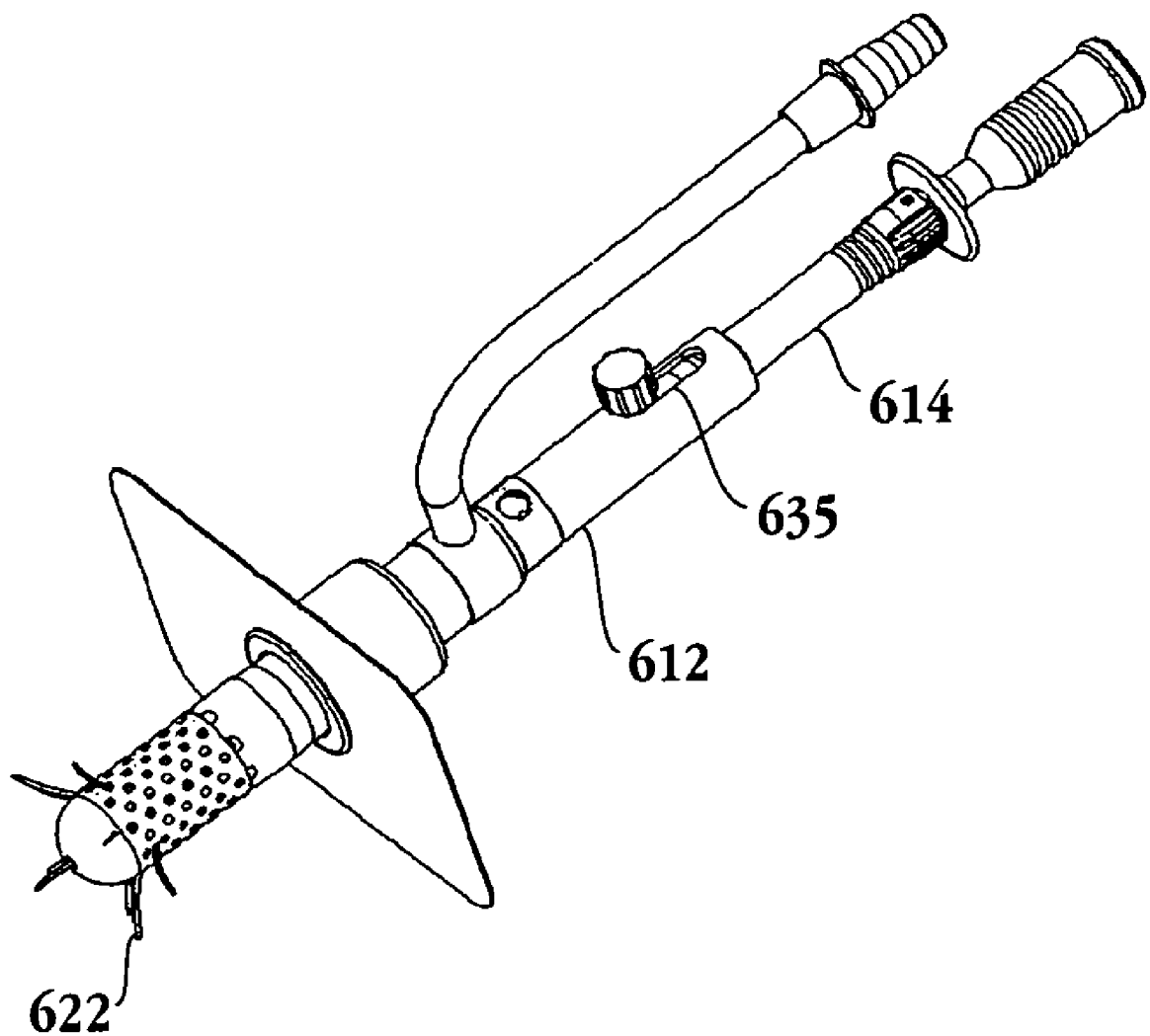

As seen in FIG. 5, the sleeve 512 may include a linear slide 535 for receiving at least a portion of the ablation device 514. In this manner the sleeve and device are engaged such that the electrodes, when deployed, are aligned with the openings in the sleeve. As seen in FIG. 6C, the linear slide 635 is positioned at the proximal portion of the sleeve 612 and preferably includes a section for entry of at least a portion of the probe 614 into the slide area. In this manner, the probe may be axially adjusted within the sleeve by movement of the probe within the slide. Deployment of the electrodes 622 from the openings in the sleeve may be reciprocally adjusted. It will be appreciated that the length of the slide may be varied based on several factors such as the length of the openings as well as the depth of the cavity.

As seen in FIG. 6A-6B, the sleeve 612 may further include a locking mechanism with two or more slots 634, 636 for receiving a portion of the device 614. The mechanism is configured to allow the physician to selectively control the amount of the probe housed in the sleeve, and thus the position of the deployment of the electrodes within the openings. In use, the physician first locks the probe in the distalmost slot 634. As seen in FIG. 6A, in this configuration, the electrodes are deployed from the distal region of the openings. This position can be used to ablate a margin of tissue near the bottom of the cavity. For longer cavities, the surgeon can then retract the electrodes and reposition the probe 614 to the proximal locking slot 636. As seen in FIG. 6B, the electrodes 622 are then deployed from a proximal region of the openings in the sleeve. The apparatus may include a plurality of slots 634, 636 to provide a range of deployment of the electrodes through the openings. It will be appreciated that the physician may position the sleeve using the slots in any sequence.

It will be appreciated that the electrodes may be deployed radially or asymmetrically depending on the position of the cavity and surrounding structures. In this manner, a variety of different geometries, not always symmetrical, can be ablated. For example, for cavities near the chest wall or other critical structures, the electrodes may be deployed to ablate only the vertical walls, or a portion thereof.

The method can further utilize, before and/or after the tumor is excised, known imaging systems such as X-ray graphs, computerized tomography, MRI, scintigraphy, or ultrasound imaging to locate one or more specific tumor areas of interest and, optionally, to map the extent of the tumor lesion.

The temperature of the tissue, the device, or of the electrodes may be monitored, and the output power of energy source adjusted accordingly. Temperature can be maintained to a certain level by having feedback control system adjust the power output automatically to maintain that level. The physician can, if desired, override the closed or open loop system.

The closed loop system can also utilize a controller to monitor the temperature, adjust the RF power, analyze the result, refeed the result, and then modulate the power. More specifically, the controller governs the power levels, cycles, and duration that the RF energy is distributed to the electrodes to achieve and maintain power levels appropriate to achieve the desired treatment objectives and clinical endpoints. The controller can be integral to or otherwise coupled to the power source. The controller can be also be coupled to an input/output (I/O) device such as a keyboard, touchpad, PDA, microphone (coupled to speech recognition software resident in the controller or other computer) and the like. After a cool-down cycle of about 30 seconds, the sensors positioned on the electrode or the sleeve may be used as an indicator of the temperature of the tissue in the feedback process. In another embodiment, a feedback control system can be operatively connected to the energy source, the at least one sensor, and the electrodes. The feedback control system receives temperature data from the sensor(s) and the amount of electromagnetic energy received by the electrodes is modified from an initial setting of ablation energy output, ablation time, temperature, and current density (the "Four Parameters") based on the data received from the sensor(s). In one embodiment, the feedback control system can automatically change any of the Four Parameters. The feedback control system may include a multiplexer (digital or analog) to multiplex different electrodes, sensors, sensor arrays, and/or a temperature detection circuit that provides a control signal representative of temperature or impedance detected at one or more sensors. A microprocessor can be connected to the temperature control circuit.

Figure 8A:
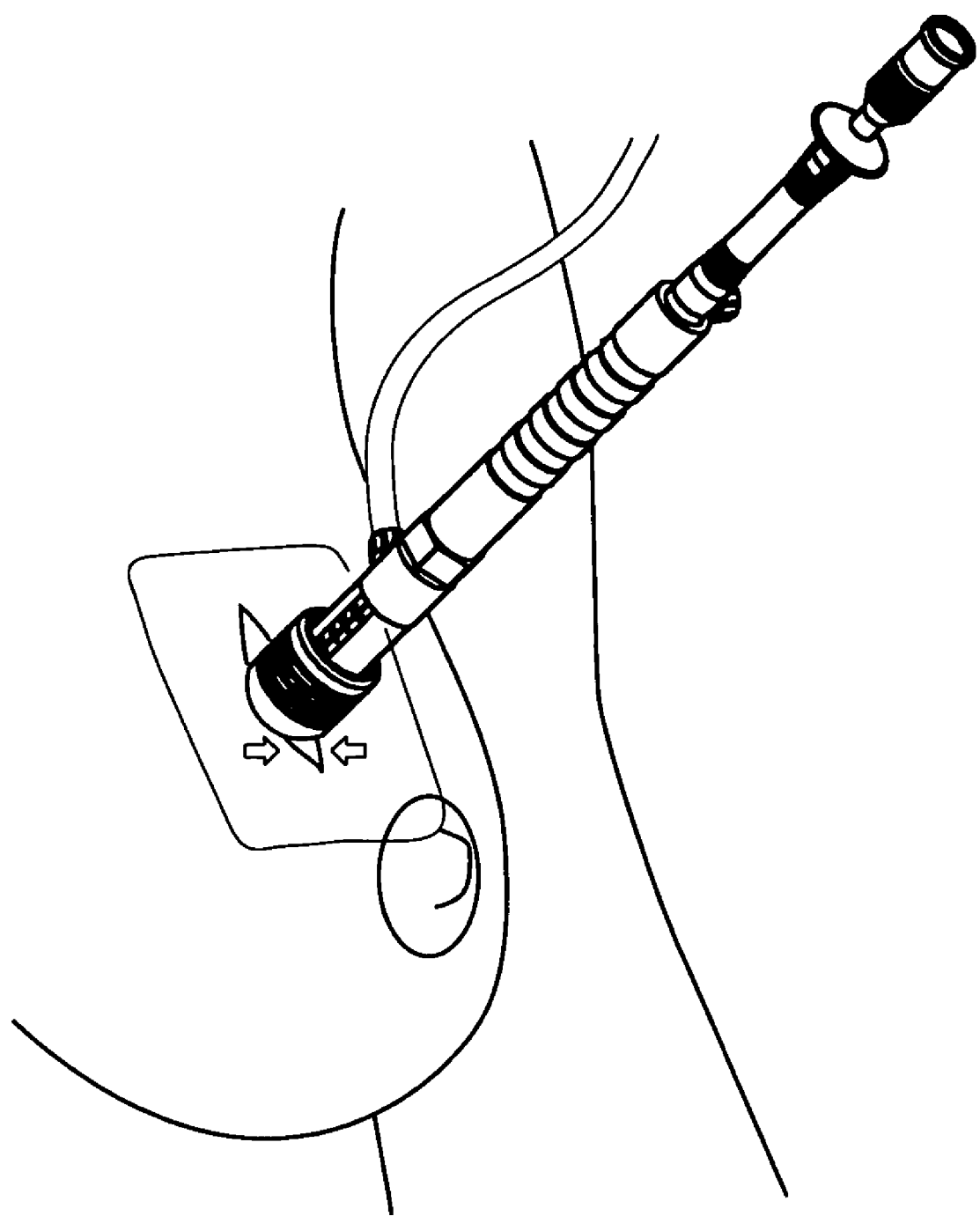
FIGS. 8A-8D show using the device for ablation of a lumpectomy cavity in a breast.
Figure 8B:
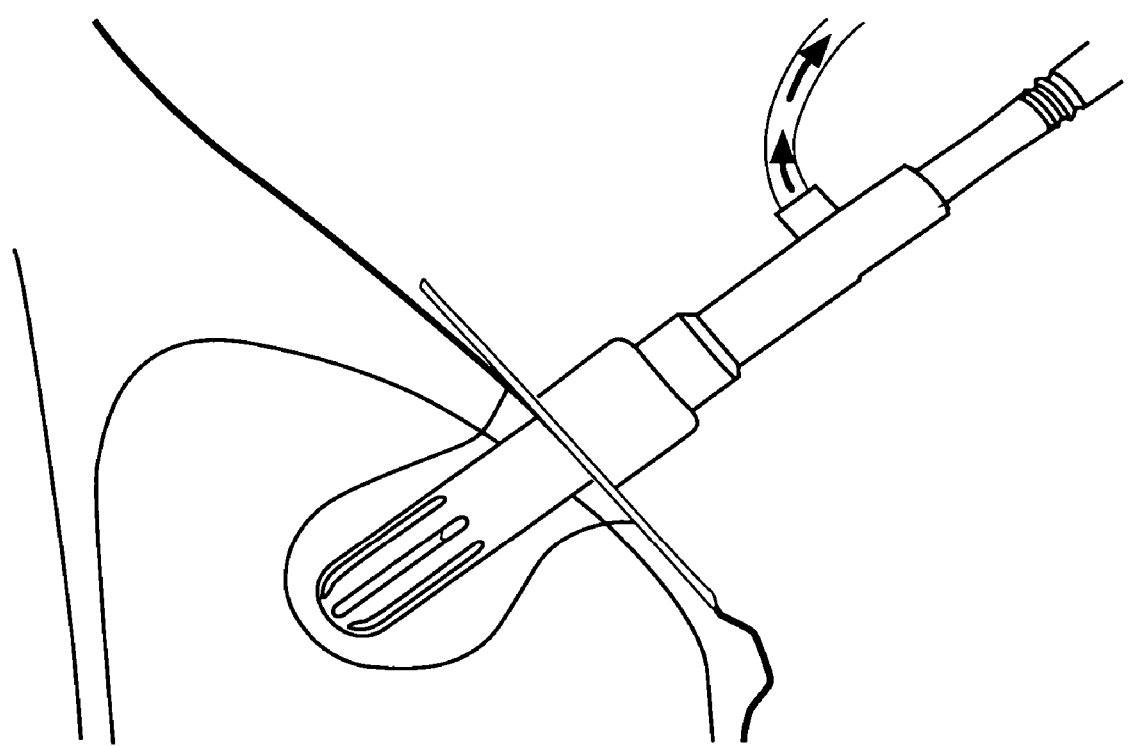
Figure 8C:
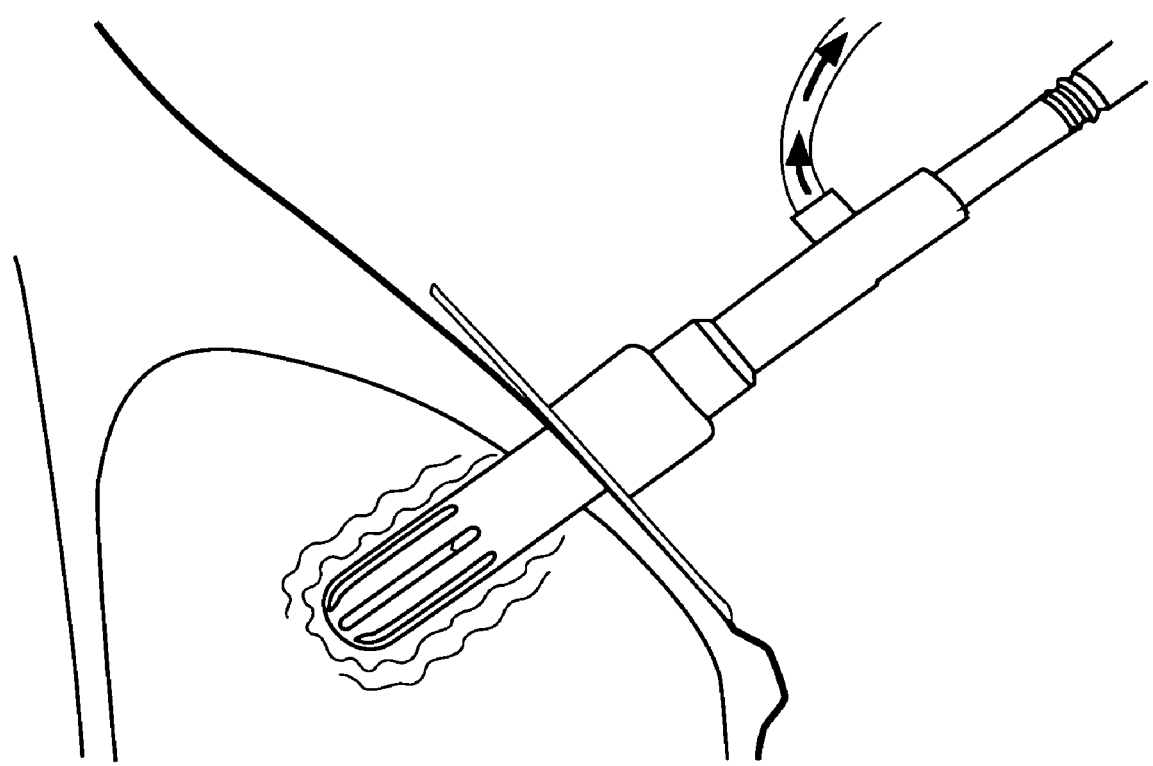
Figure 8D:
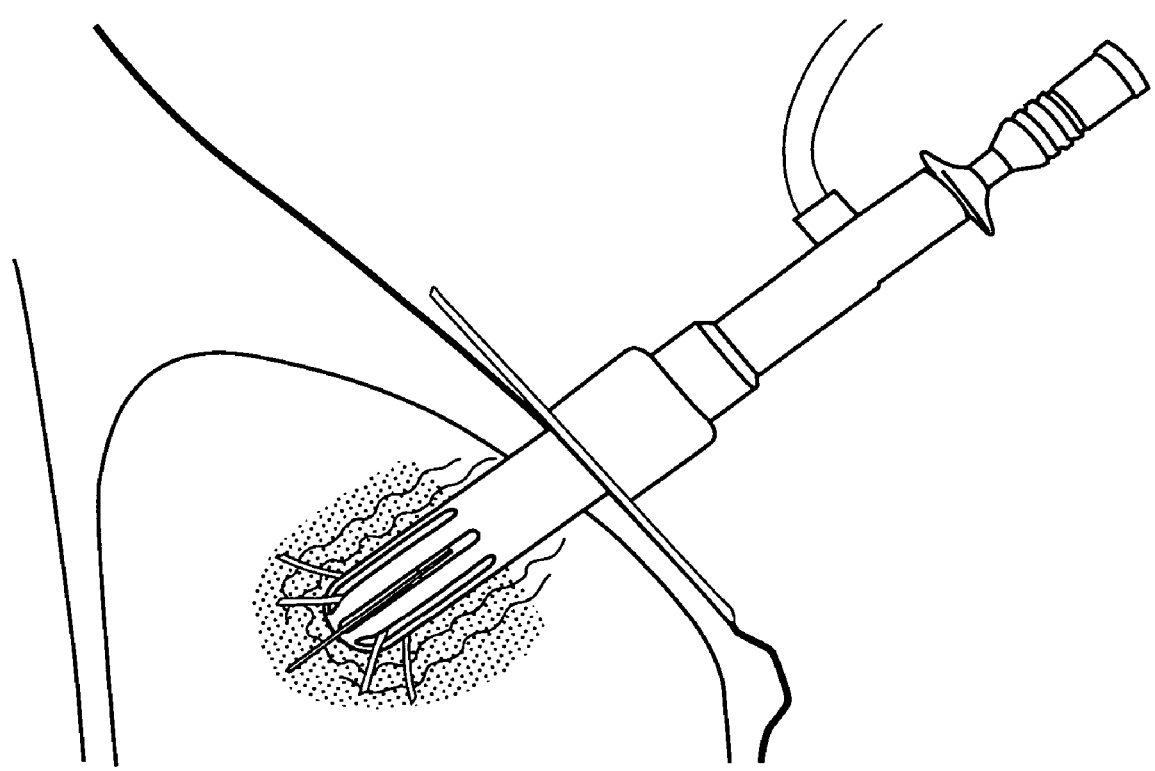

As seen in FIGS. 8A-8D, the method of the invention is well suited for ablation of surgical cavities in the breast, especially lumpectomy cavities. According to the ACS, the use of breast-conserving surgeries now accounts for nearly ½ of all the breast cancer surgeries performed in the U.S. each year. There are approximately 150,000-170,000 lumpectomies performed per year in the US. In this method, the apparatus is positioned at least partially in the lumpectomy cavity (FIG. 8A). In a preferred embodiment, the distal end of the apparatus is placed at or near the bottom of the surgical cavity. The sealing plate may be axially adjusted on the sleeve or probe such that the sealing plate is adjacent the surface of the breast. Suction is then applied to the suction port at the sleeve and/or plate, which creates a vacuum in the cavity (FIG. 8B). Application of suction is effective to draw the tissue surrounding the cavity into contact with the surface of the sleeve (FIG. 8C). At least one electrode is deployed from the apparatus through at least one opening in the sleeve distal region and activated to ablate a margin of tissue surrounding the surgical cavity (FIG. 8D). The electrode(s) are retracted and the device is withdrawn from the cavity. It will be appreciated that before withdrawing the device from the cavity, the electrodes may be deployed at different axial positions within the cavity to achieve a margin of ablated tissue along a desired length of the cavity. This is especially useful for longer cavities.

With Breast Conserving Surgery (BCS) the tumor is removed along with a variable margin of tissue, usually about 1 cm, surrounding the tumor. The margin is then assessed for malignant cells. If there are no malignant cells in the margin (negative margin), the surgery is considered to have removed all cancerous tissue. The majority of the breast is left in tact, and depending on the amount of tissue spared, cosmetic results are usually satisfactory.

However, if the margin includes malignant cells near the tissue edge (close margin) or even at the tissue edge (negative margin), the patient must endure a second surgery to remove more tissue.

Using the present method, the need for additional surgery is reduced or eliminated. Another benefit of the present method is a known margin of ablated tissue at least partially surrounding the cavity. This ablated margin is usually in addition to the margin of tissue resected around the tumor. As detailed in Example 1, the apparatus was used to ablate a cavity formed in breast tissue. Briefly, the apparatus was placed in a cavity formed in breast tissue obtained from a mastectomy. The sealing member was adjusted to a position adjacent the tissue surface and suction was applied to the sleeve at the port. The tissue was drawn against the sleeve with no voids visible upon inspection through the sealing plate. The electrodes were deployed into the tissue surrounding the cavity and activated to form a margin of ablated tissue surrounding the cavity. After the procedure, the tissue appeared to be necrosed and coagulated, indicating the tissue was successfully ablated.

In another aspect, the method may be used for asymmetric ablation of a cavity wall, or a particular area of a cavity wall. In this embodiment, the cavity may be a surgical cavity or a body cavity. In this embodiment, the apparatus includes a tissue contacting surface adapted to be placed adjacent or against the treatment site. In one embodiment, the apparatus may be thermally insulated to reduce or prevent ablation of undesired tissue in the cavity. The tissue contacting surface may further include a suction port or suction cup for affixing the tissue contacting surface to the treatment site or holding the treatment site to the tissue contacting surface of the apparatus. In this manner the tissue may be fixed to the apparatus and held stable for insertion of the electrodes to the target tissue. At least one electrode is deployed from the tissue contacting surface into the tissue to be treated and activated to produce an ablated tissue margin surrounding the at least one electrode. In this manner, the cavity wall can be selectively ablated. It will be appreciated this embodiment may be useful for treatment of esophageal cancer, uterine fibroids, cysts, a tumor with a necrotic core, and colon polyps, among others. It will be appreciated that the device may be used in any body or surgical cavity where ablation of the cavity margins is desired. In another embodiment, the device may be used for ablation of a tubular cavity such as a vessel or duct. For this embodiment, the device may further include a deployable or inflatable section distal to the activating structure to seal the cavity. An exemplary structure is an expandable balloon that can be deployed distal to the probe to seal the tubular cavity such that suction can be used to draw the tissue of the tubular cavity to the probe. The device may also include a barrier at the proximal end of the probe to seal the tubular cavity proximal to the probe. In an exemplary embodiment, the apparatus may include a deployable stent at the distal end for use in treating an aneurysm. In this embodiment, the probe is deployed into the vessel and at least one barrier is deployed distal to the probe distal end to seal the vessel. Suction is used to draw the tissue of the tubular cavity to the probe and the electrode(s) are deployed and activated to collapse the aneurysm. The probe is removed leaving the stent in situ. It will be appreciated that the stent may become affixed to the cavity tissue during ablation and/or a suitable adhesive may be used to affix the stent to the tissue site.

EXAMPLES

The following example illustrates but is in no way intended to limit the invention.

Example 1

Ablation of Margins in Breast Tissue

A section of tissue was excised from breast tissue obtained from a mastectomy. The apparatus was positioned in the cavity such that the distal end of the sleeve contacted the bottom of the cavity. The sealing plate was adjusted adjacent the tissue surface and suction was applied using a surgical suite available vacuum supply. The walls of the cavity were drawn against the distal end of the sleeve and no voids were visible through the sealing plate. Electrodes were deployed into the tissue and activated to a target temperature of 100° C. After 15 minutes at the target temperature, the tissue was visually inspected and determined to be coagulated and necrosed. Indicators of tissue necrosis included a visual change in the coloration and texture of the tissue and/or a temperature above 70° C. 30 seconds after cease of electrode activation. It will be appreciated that other methods of visualizing cell death are suitable including the use of dyes and stains that have phallic properties to dead cells.

It will be appreciated that embodiments described with respect to one aspect may be applicable to each aspect of the device and method described. As a non-limiting example, the thermal barrier may be used with the elongate sleeve as well as with an integral probe. It will further be appreciated that embodiments may be used in combination or separately. It will also be realized that sub-combinations of the embodiments may be used with the different aspects. Thus, although embodiments have been described with many optional features, these features are not required unless specifically stated.

It will also be realized that the apparatus may be used in combination with other procedures or methods as appropriate. For example, the apparatus may be used in conjunction with chemotherapy, surgery, and/or a thermally activated therapeutic agent.

The foregoing description provides specific details for an understanding of, and enabling description for, embodiments of the apparatus. However, one skilled in the art will understand that the invention may be practiced without these details. In other instances, well-known structures and functions have not been shown or described in detail to avoid unnecessarily obscuring the description of the embodiments of the invention.

It is claimed:
1. A method for ablating margins of a surgical cavity formed in a tissue, comprising:
   (a) inserting an elongate apparatus into an opening of the surgical cavity formed from a surgical procedure, wherein the elongate apparatus includes a radially extending sealing member;
   (b) advancing the elongate apparatus into the surgical cavity until the sealing member presses against the surface of skin surrounding the opening of the surgical cavity to cover the opening of the surgical cavity;
   (c) applying suction at surface regions of the advanced elongate apparatus within the surgical cavity, thereby to draw wall portions of the tissue into contact with said elongate apparatus surface regions, wherein tissue margins in the surgical cavity surround the apparatus, and (d) while maintaining suction at said surface regions, ablating said tissue margins.

2. The method of claim 1, wherein step (d) includes (di) introducing one or more electrodes into said tissue margins, and (dii) applying radiofrequency or microwave power to said electrodes until said margins have been ablated.

3. The method of claim 2, wherein step (di) includes deploying a plurality of electrodes into said margins at radially spaced intervals that, with the application of radiofrequency power to the electrodes in step (dii) define an ablation volume surrounding said apparatus and including said margins.

4. The method of claim 3, wherein said apparatus includes a plurality of radially spaced openings through which suction is applied to said surface region, and said electrodes are deployed through said openings in step (di).

5. The method of claim 1, further comprising:
provid ing air flow from the surgical cavity through a vent positioned in the apparatus at a position outside the surgical cavity.

6. The method of claim 1, further comprising:
(e) discontinuing the suction;
(f) repositioning the position of the elongate apparatus within the surgical cavity and repeating steps (a)-(d).

7. A method for ablating margins of a surgical cavity formed in a tissue, comprising:
(a) performing a surgical procedure that creates a surgical cavity having an opening at the skin;
(b) inserting an elongate apparatus into the opening of the surgical cavity, wherein the elongate apparatus includes a radially extending sealing plate;
(c) advancing the elongate apparatus into the surgical cavity until the sealing plate presses against the surface of skin surrounding the opening of the surgical cavity to cover the opening of the surgical cavity;
(d) applying suction at surface regions of the advanced elongate apparatus within the surgical cavity, thereby to draw wall portions of the tissue into contact with said elongate apparatus surface regions, wherein tissue margins in the surgical cavity surround the apparatus; and
(e) while maintaining suction at said surface regions, ablating said tissue margins.

8. The method of claim 7, wherein step (e) includes (ei) introducing one or more electrodes into said tissue margins, and (eii) applying radiofrequency or microwave power to said electrodes until said margins have been ablated.

9. The method of claim 8, wherein step (ei) includes deploying a plurality of electrodes into said margins at radially spaced intervals that, with the application of radiofrequency power to the electrodes in step (eii) define an ablation volume surrounding said apparatus and including said margins.

10. The method of claim 9, wherein said apparatus includes a plurality of radially spaced openings through which suction is applied to said surface region, and said electrodes are deployed through said openings in step (ei).

11. The method of claim 7, further comprising:
providing air flow from the surgical cavity through a vent positioned in the apparatus at a position outside the surgical cavity.

12. The method of claim 7, further comprising:
(f) discontinuing the suction;
(g) repositioning the position of the elongate apparatus within the surgical cavity and repeating steps (b)-(e).

* * * * *